US008414903B2

(12) United States Patent
Waldor et al.

(10) Patent No.: US 8,414,903 B2
(45) Date of Patent: Apr. 9, 2013

(54) ***ESCHERICHIA COLI* MUTANTS AND METHODS OF USE THEREOF**

(75) Inventors: Matthew K. Waldor, Newton, MA (US); Theresa D. Ho, Iowa City, IA (US)

(73) Assignee: Tufts University, Boston, MA (US)

( * ) Notice: Subject to any disclaimer, the term of this patent is extended or adjusted under 35 U.S.C. 154(b) by 0 days.

(21) Appl. No.: 12/312,739

(22) PCT Filed: Nov. 20, 2007

(86) PCT No.: PCT/US2007/024279
§ 371 (c)(1),
(2), (4) Date: Dec. 23, 2009

(87) PCT Pub. No.: WO2008/133659
PCT Pub. Date: Nov. 6, 2008

(65) Prior Publication Data
US 2010/0092511 A1 Apr. 15, 2010

Related U.S. Application Data

(60) Provisional application No. 60/861,944, filed on Nov. 29, 2006.

(51) Int. Cl.
*A61K 39/108* (2006.01)
*A61K 39/02* (2006.01)
*A01N 63/00* (2006.01)
*C12P 21/04* (2006.01)
*C12N 15/09* (2006.01)

(52) U.S. Cl. ............... 424/257.1; 424/200.1; 424/234.1; 424/93.2; 424/93.48; 424/823; 435/71.1; 435/69.3

(58) Field of Classification Search .................. None
See application file for complete search history.

(56) References Cited

U.S. PATENT DOCUMENTS
2002/0160020 A1 10/2002 Finlay et al.

FOREIGN PATENT DOCUMENTS
WO WO97/40063 A2 10/1997
WO WO99/24576 A1 5/1999
WO WO 2006047517 * 5/2006

OTHER PUBLICATIONS

Kariyawasam et al. Avian Diseases 48: 287-299, 2004.*
Woodward et al. Int. J. Med. Microbiol. 293: 299-308, Aug. 2003.*
Baba et al. "Construction of *Escherichia coli* K-12 in-frame, single-gene knockout mutants: the Keio collection," Mol Syst Biol, Feb. 21, 2006, vol. 2, pp. 1-11; doi: 10.1038/msb4100050.
Bilge et al. "Role of the *Echerichia coli* O157: H7 O Side Chain in Adherence and Analysis of an rfb Locus," Infect Immun, Nov. 1996, vol. 64, No. 11, pp. 4795-4801; American Society for Microbiology.
Calhoun et al. "*Salmonella*-based plague vaccines for bioterrorism," J Microbiol Immunol Infect, Apr. 2006, vol. 39, No. 2, pp. 92-97; Elsevier.
Canny et al. "Lipid mediator-induced expression of bactericidal/permeability-increasing protein (BPI) in human mucosal epithelia," Pro Natl Sci Acad, Mar. 19, 2002, vol. 99, No. 6, pp. 3902-3907; doi/10.1073/pnas.052533799.
Chiang et al. "rfb Mutations in Vibrio cholerae Do Not Affect Surface Production of Toxin-Coregulated Pili but Still Inhibit Intestinal Colonization," Infect Immun, Feb. 1999, vol. 67, No. 2, pp. 976-980; American Society for Microbiology.
Cockerill et al. "Polysaccharide Side Chains Are Not Required for Attaching and Effacing Adhesion of *Escherichia coli* O157: H7," Infect Immun, Aug. 1996, vol. 64, No. 8, pp. 3196-3200; American Society for Microbiology.
Datsenko et al. "One-step inactivation of chromosomal genes in *Escherichia coli* K-12 PCR products," Proc Natl Acad Sci, Jun. 6, 2000, vol. 97, No. 12, pp. 6640-6645; National Academy of Sciences, Washington D.C.
Donnenberg "Infections Due to *Escherichia coli* and Other Enteric Gram-Negative *Bacilli*," Chapter 138 in ACP Medicine Principles and Practice 2007, Jul. 2007, pp. 1626-1633; BC Decker.
Dorsey et al. "Directed delivery of heat-labile enterotoxin by enterotoxigenic *Escherichia coli*," Cell Microbiol, May 16, 2006, vol. 8, iss 9, pp. 1516-1527; doi:10.1111/j.1462-5822.2006.00736x.
Evans et al. "Virulence Factors of Enterotoxigenic *Escherichia coli*," J Infect Disease, Aug. 1977, vol. 136, suppl, pp. S118-S123; The University of Chicago Press.
Feng et al., "*Escherichia coli*," Chapter 10 in Guide to Foodborne Pathogens, 2001; edited by Labibe et al., John Wiley & Sons, Inc.
Gazzano-Santoro et al. "High- Affinity Binding of the Bactericidal/Permeability-Increasing Protein and a Recombinant Amino-Terminal Fragment to the Lipid A Region of Lipopolysaccharide," Infect Immun, Nov. 1992, vol. 60, No. 11, pp. 4754-4761; American Society for Microbiology.
Genevaux et al. "Identification of Tn10 insertions in the rfaG, rfaP, and galU genes involved in lipopolysaccharide core biosynthesis that affect *Escherichia coli* adhesion," Arch Microbiol, Jun. 1999, vol. 172, iss 1, pp. 1-8; doi: 10.1007/s002030050732.
Gilman et al., "Evaluation of a UDP-Glucose-4-Epimeraseless Mutant of *Salmonella typhi* as a Live Oral Vaccine," Infect Disease, Dec. 1977, vol. 136, No. 6, pp. 717-723; University of Chicago Press.
Gray et al. "Bactericidal Activity of Synthetic Peptides Based on the Structure of the 55-Kilodalton Bactericidal Protein from Human Neutrophils," Jul. 1994, vol. 62, No. 7, pp. 2732-2739; American Society for Microbiology.
Haldimann et al. "Conditional-Replication, Integration, Excision, and Retrieval Plasmid-Host Systems for Gene Structure-Function Studies of Bacteria," J Bacteriol, Nov. 2001, vol. 183, No. 21, pp. 6384-6391; doi: 10.1128/JB.183.21.6384-6393.2001.
Ho et al. "Enterohemorrhagic *Escherichia coli* O157:H7 gal Mutants Are Sensitive to Bacteriophage P1 and Defective in Intestinal Colonization," Infect Immun, Apr. 2007, vol. 75, No. 4, pp. 1661-1666; doi:10.1128/IAI.01342-06.

(Continued)

*Primary Examiner* — S. Devi
(74) *Attorney, Agent, or Firm* — Lawson & Weitzen, LLP; Sonia K. Guterman; Teofilo Javier, Jr.

(57) ABSTRACT

The present invention provides methods and compositions for production of gram-negative bacterial mutants that are defective in intestinal colonization capacity and sensitive to infection by bacteriophage P1. Thus the present invention provides immunogenic compositions for the prevention or attenuation of food- and water-borne illnesses associated with ingestion of bacteria such as enterohemorrhagic *Escherichia coli*.

9 Claims, 2 Drawing Sheets

OTHER PUBLICATIONS

Hohmann et al. "Intestinal and Serum Antibody Responses in Mice After Oral Immunization with *Salmonella*, *Escherichia coli*, and *Salmonella-Escherichia coli* Hybrid Strains," Infect Immun, Jul. 1979, vol. 25, No. 1, pp. 27-33; American Society for Microbiology.

Jerse et al. "A genetic locus of enteropathogenic *Escherichia coli* necessary for the production of attaching and effacing lesions on tissue culture cells," Proc Natl Acad Sci, Oct. 1990, vol. 87, pp. 7839-7843; National Academy of Sciences, Washington D.C.

Karmali "Infection by Verocytotoxin-Producing *Escherichia coli*," Clin Microbiol Rev, Jan. 1989, vol. 2, No. 1, pp. 15-38; American Society for Microbiology.

Ll et al. "Human Response to *Escherichia coli* O157:H7 Infection: Antibodies to Secreted Virulence Factors," Infect Immun, Sep. 2000, vol. 68, No. 9, pp. 5090-5095; American Society for Microbiology.

Little et al. "Functional Domains of Recombinant Bactericidal/Permeability Increasing Protein (rBPI23)," J Biol Chem, Jan. 21, 1994, vol. 269, No. 3, pp. 1865-1872; American Society for Biochemistry and Molecular Biology,Inc.

McCallum et al. "A High-Molecular-Weight Fraction of Smooth Lipopolysaccharide in Klebsiella Serotype O1: K20 Contains a Unique O-Antigen Epitope and Determines Resistance to Nonspecific Serum Killing," Infect Immun, Dec. 1989, vol. 57, No. 12, pp. 3816-3822; American Society for Microbiology.

Mead et al. "Food-related illness and death in the United States" Emerg Infect Diseas, Sep.-Oct. 1999, vol. 5, No. 5, pp. 607-625; Centers for Disease Control and Prevention.

Miller et al. "A Novel Suicide Vector and Its Use in Construction of Insertion Mutations: Osmoregulation of Outer Membrane Proteins and Virulence Determinants in Vibrio cholerae Requires toxR" J Bacteriol, Jun. 1988, vol. 170, No. 6, pp. 2575-2583; American Society for Microbiology.

Mulvey et al. "Establishment of a Persistent *Escherichia coli* Reservoir during the Acute Phase of a Bladder Infection" Infect Immun, Jul. 2001, vol. 69, No. 7, pp. 4572-4579; doi: 10.1128/IAI.69.7.4572-4579.2001.

Nesper et al. "Characterization of *Vibrio cholerae* O1 El Tor galU and galE Mutants: Influence on Lipopolysaccharide Structure, Colonization, and Biofilm Formation," Infect Immun, Jan. 2001, vol. 69, No. 1, pp. 435-445; doi: 10.1128/IAI.69.1.435-445.2001.

Ornellas et al. "Relation of Lipopolysaccharide Character to P1 Sensitivity in *Salmonella typhimurium*," Virol, Aug. 1974,vol. 60, pp. 491-502; doi: 10.1016/0042-6822(74)90343-2.

Paton et al. "Antibodies to lipopolysaccharide block adherence of Shiga toxin-producing *Escherichia coli* to human intestinal epithelial (Henle 407) cells" Microbial Pathogenesis, Jan. 1998, vol. 24, pp. 57-63; doi: 10.1006/mpat.1997.0172.

Paton et al. "Pathogenesis and Diagnosis of Shiga Toxin-Producing *Escherichia coli* Infections," Clin Microbiol Rev, Jul. 1998, vol. 11, No. 3, pp. 450-479; American Society for Microbiology.

Perna et al. "Genome sequence of enterohaemorrhagic*Escherichia coli* O157:H7," Nature, Jan. 25, 2001, vol. 409, pp. 529-533; doi:10.1038/35054089.

Perna et al., NCBI Reference Sequence: NC_002655.2; Sequence first published in "Genome sequence of enterohaemorrhagic *Escherichia coli* O157:H7," Nature, Jan. 25, 2001, vol. 409, pp. 529-533; doi 10.1038/35054089 (p. 1 of 899 submitted here).

Perna et al., NCBI Reference Sequence: NP_286478.1; Sequence first published in "Genome sequence of enterohaemorrhagic *Escherichia coli* O157:H7," Nature, Jan. 25, 2001, vol. 409, pp. 529-533; doi 10.1038/35054089.

Perna et al., NCBI Reference Sequence: NP_286479.1; Sequence first published in "Genome sequence of enterohaemorrhagic *Escherichia coli* O157:H7," Nature, Jan. 25, 2001, vol. 409, pp. 529-533; doi 10.1038/35054089.

Perna et al., NCBI Reference Sequence: NP_286480.1; Sequence first published in "Genome sequence of enterohaemorrhagic *Escherichia coli* 157:H7," Nature, Jan. 25, 2001, vol. 409, pp. 529-533; doi 10.1038/35054089.

Perna et al., NCBI Reference Sequence: N_286976.1; Sequence first published in "Genome sequence of enterohaemorrhagic *Escherichia coli* O157:H7," Nature, Jan. 25, 2001, vol. 409, pp. 529-533; doi 10.1038/35054089.

Perna et al., NCBI Reference Sequence: NP_287481.1; Sequence first published in "Genome sequence of enterohaemorrhagic *Escherichia coli* O157:H7," Nature, Jan. 25, 2001, vol. 409, pp. 529-533; doi 10.1038/35054089.

Perna et al., NCBI Reference Sequence: NP_288673.1; Sequence first published in "Genome sequence of enterohaemorrhagic *Escherichia coli* O157:H7," Nature, Jan. 25, 2001, vol. 409, pp. 529-533; doi 10.1038/35054089.

Peschel et al. "How do bacteria resist human antimicrobial peptides?" Trends in Microbiol, Apr. 2002, vol. 10, No. 4, pp. 179-186; doi:10.1016/S0966-842X(02)02333-8.

Perry et al. "Structure of the O-chain polysaccharide of the phenol-phase soluble lipopolysaccharide of *Escherichia coli* O:157: H7," Biochem Cell Biol, Jan. 1, 1986, vol. 64, pp. 21-28; NRC Research Press, Ottowa, Canada.

Pluschke et al. "Degree of Antibody-Independent Activation of the Classical Complement Pathway by K1 *Escherichia coli* Differs with O Antigen Type and Correlates with Virulence of Meningitis in Newborns," Infect Immun, Feb. 1984, vol. 43, No. 2, pp. 684-692; American Society for Microbiology.

Raetz et al. Chapter 69, "Bacterial Lipopolysaccharides: a Remarkable Family of Bioactive Macroamphiphiles," pp. 1035-1063, in *Escherichia coli* and *Salmonella*, vol. 1, ed. by Neidhart, 1996; ASM Press.

Rajashekara et al. "Attenuated Bioluminescent *Brucella melitensis* Mutants GR019 (virB4), GR024 (galE), and GR026 (BMEI1090-BMEI1091) Confer Protection in Mice," Infect Immun, May 2006, vol. 74, No. 5, pp. 2925-2936; doi: 10.1128/IAI.74.5.2925-2936.2006.

Ritchie et al. "Critical Roles for stx2,eae, and tir in Enterohemorrhagic *Escherichia coli*-Induced Diarrhea and Intestinal Inflammation in Infant Rabbits," Infect Immun, Dec. 2003, vol. 71, No. 12, pp. 7129-7139; doi: 10.1128/IAI.71.12.7129-7139.2003.

Sandkvist "Type II Secretion and Pathogenesis," Infect Immun, Jun. 2001, vol. 69, No. 6, pp. 3523-3535; doi: 10.1128/IAI.69.6.3523-3535.2001.

Singer et al. "A Collection of Strains Containing Genetically Linked Alternating Antibiotic Resistance Elements for Genetic Mapping of *Escherichia coli*," Microbiol Rev, Mar. 1989, vol. 53, No. 1, pp. 1-24; American Society for Microbiology.

Winter et al. "Man-made antibodies," Nature, Jan. 24, 1991, vol. 349, pp. 293-299; doi:10.1038/349293a0.

* cited by examiner

FIG. 1

A. Δ*galETKM*::*aad*-7(TEA026) versus wild type(EDL933)

B. Δ*galETKM*::*aad*-7(TEA026) versus Gal+ revertant(TEA040)

FIG. 2

A. Generate x::ab^R in a TEA028 derivative.

B. Make P1 lysate on mutant and move x::ab^R by P1 transduction into TEA007.

C. Move galETKM+ from TEA023 by P1 transduction into x::ab^R galE::pTHE001 strain.

ESCHERICHIA COLI MUTANTS AND METHODS OF USE THEREOF

RELATED APPLICATIONS

The present application claims the benefit of U.S. provisional patent application Ser. No. 60/861,944, filed Nov. 29, 2006 in the U.S. Patent and Trademark Office, and international application serial number PCT/US2007/024279 filed 20 Nov. 2007 in the PCT Receiving Office of the United State Patent and Trademark Office.

GOVERNMENT SUPPORT

This invention was made with government support under grant A1067827 awarded by the National Institutes of Health. The government has certain rights in this invention.

The invention was made in part with support from NIH R21A1067827. The government has certain rights in the invention.

FIELD OF THE INVENTION

The present invention provides methods and compositions for production of gram-negative bacterial mutants that are defective in intestinal colonization capacity and sensitive to infection by bacteriophage P1. Thus the present invention provides immunogenic compositions for the prevention or attenuation of food- and water-borne illnesses associated with ingestion of bacteria such as enterohemorrhagic *Escherichia coli*.

BACKGROUND OF THE INVENTION

Enterohemorrhagic *Escherichia coli* (EHEC) is an emerging food- and water-borne pathogen that colonizes the distal ileum and colon and produces potent cytotoxins (Donnenberg, "Infections due to *Escherichia coli* and other enteric gram-negative bacilli," in *ACP Medicine*, WebMD Professional Publishing, Danbury Conn., Chapter 7, pp. 8-1 to 8-18, 2005). After ingestion of contaminated food, humans can develop symptoms ranging from mild diarrhea to the severe, and at times life-threatening, hemolytic uremic syndrome (HUS). Currently, EHEC is the most common cause of pediatric renal failure in the United States (Mead et al., *Emerg Infect Dis*, 5:607-625, 1999). Several EHEC serotypes cause disease, but the O157 serotype is by far the most common cause of EHEC-related disease in North America, Europe and Japan (Feng, "*Escherichia coli*," in Garcia (ed.) *Guide to Foodborne Pathogens*, John Wiley and Sons, Inc., pp. 143-162, 2001).

EHEC O157:H7 colonization of healthy cattle remains a serious public health threat due to the low numbers of EHEC O157:H7 (e.g., 10-100) necessary to infect a human and to the bulk processing of slaughtered cattle. Methods for detecting and subsequently killing EHEC O157:H7 at slaughter, altering the diet of cattle to reduce the number of intestinal EHEC O157:H7 and immunizing animals to prevent EHEC O157:H7 colonization are being employed to address this problem. Recently, the recombinant production and use of EHEC O157:H7 proteins including recombinant EspA (International Publication No. WO 97/40063), recombinant TIR (International Publication No. WO 99/24576), recombinant EspB and recombinant Initimin (Li et al., *Infec Immun*, 68:5090-5095, 2000) have been described. However, production and purification of recombinant proteins in amounts sufficient for use as antigens is difficult and expensive.

Thus there is a need in the art for compositions and method for blocking EHEC O157:H7 colonization of cattle and other mammals and, thereby, for reducing shedding of EHEC into the environment. These tools are contemplated to be useful for reduce the incidence of health problems associated with EHEC-contaminated meat and water.

SUMMARY OF THE INVENTION

The present invention provides methods and compositions for production of gram-negative bacterial mutants that are defective in intestinal colonization capacity and sensitive to infection by bacteriophage P1. Thus the present invention provides immunogenic compositions for the prevention or attenuation of food- and water-borne illnesses associated with ingestion of bacteria such as enterohemorrhagic *Escherichia coli*.

In particular the present invention provides an isolated *Escherichia coli* (*E. coli*) bacterium comprising an inactivating mutation in one or more galactose-modifying enzymes. In some embodiments, the galactose-modifying enzymes are selected from the group consisting of GalE, GalT, GalK and GalU. In preferred embodiments, *E. coli* is selected from the group consisting of enterohemorrhagic *E. coli* (EHEC), enteropathogenic. *E. coli* (EPEC), enterotoxigenic *E. coli* (ETEC) and uropathogenic *E. coli* (UPEC). In a subset of these embodiments, the EHEC is *E. coli* O157. In some preferred embodiments, the *E. coli* O157 is serotype O157:H7. In some particularly preferred embodiments, the *E. coli* O157 is of a strain selected from the group consisting of TEA007 (galE::pTHE001), TEA023 (ΔgalU::aad-7), TEA026 (ΔgalETKM::aad-7) and TEA028 (ΔgalETKM::tetA). In preferred embodiments, the inactivating mutation is associated with one or more of reduced O-antigen expression, with increased susceptibility to bacteriophage P1, with increased sensitivity to bactericidal/permeability-increasing protein (BPI) and reduced intestinal colonization. In some embodiments, the BPI comprises the amino acid sequence of peptide P2 set forth as SEQ ID NO:9. The present invention also provides *E. coli* bacterium further comprising an inactivating mutation in one or both of a shiga toxin A subunit and a shiga toxin B subunit. In some embodiments, the shigatoxin A subunit is selected from the group consisting of Stx1A and Stx2A. In some preferred embodiments, the *E. coli* bacterium further comprises a heterologous antigen. In particularly preferred embodiments, the heterologous antigen comprises a protein encoded by a bacterial, viral or protozoal pathogen, which in some embodiments is a human pathogen. Exemplary heterologous antigens include but are not limited to cholera antigens; HIV-1 antigens and *Toxoplasma gondii* antigens. In a subset of these embodiments, the *E. coli* bacterium comprises a live bacterial culture.

In addition the present invention provides compositions comprising an *E. coli* bacterium comprising an inactivating mutation in one or more galactose-modifying enzymes, suspended in an adjuvant or an excipient. In preferred embodiments, the *E. coli* bacterium further comprises an inactivating mutation in one or both of a shiga toxin A subunit and a shiga toxin B subunit, Furthermore the present invention provides methods for inducing an immune response comprising administering the claimed compositions to a subject under conditions suitable for inducing an immune response against the *E. coli* bacterium. In some embodiments, the administering is done orally or intrarectally. In some preferred embodiments, the subject is a human, while in others the subject is a ruminant. In particularly preferred embodiments, the ruminant is a bovine subject.

Moreover the present invention provides methods for reducing intestinal colonization of EHEC in a subject comprising administering a composition comprising an *E. coli* bacterium comprising an inactivating mutation in one or more galactose-modifying enzymes, and an inactivating mutation in one or both of a shiga toxin A subunit and a shiga toxin B subunit, to the subject under conditions suitable for reducing intestinal colonization. In some preferred embodiments, the subject is a human, while in others the subject is a ruminant. In preferred embodiments, the intestinal colonization comprises one or more of ileum colonization, mid-colon colonization and cecum colonization.

The present invention also provides methods for reducing fecal shedding of EHEC by a subject comprising administering a composition comprising an *E. coli* bacterium comprising an inactivating mutation in one or more galactose-modifying enzymes, and an inactivating mutation in one or both of a shiga toxin A subunit and a shiga toxin B subunit, to the subject under conditions suitable for reducing fecal shedding. In some preferred embodiments, the subject is a human, while in others the subject is a ruminant.

DESCRIPTION OF THE FIGURES

FIG. 1 depicts the results of in vivo and in vitro competition assays of an EHEC galETKM− mutant (TEA026) versus wild type (EDL933) or versus a Gal+ revertant of TEA026 (TEA040). In FIG. 1A equal numbers of TEA026 and EDL933 and in FIG. 2B equal numbers of TEA026 and TEA040 were co-inoculated into infant rabbits or into LB. After seven days of infection, sections of the ileum, mid-colon and cecum and samples of the stool were processed to determine competitive indeces. The in vitro competition assays in LB were carried out for 16 hours. Competitive Index=[(number of mutant bacteriaoutput)/(number of wild type or revertant bacteriaoutput)]/[(number of mutant bacteriainput)/(number of wild type or revertant bacteriainput)]. Each of the competitive indeces shown is statistically different from 1 ($p<0.00001$ using the student's t-test).

FIG. 2 illustrates an exemplary scheme for P1-facilitated genetic engineering of EHEC. FIG. 2A shows the construction of the desired mutation in the ΔgalETKM::tetA or ΔgalETKM::aad-7 background (e.g. using the lambda red recombination system as shown in the figure) so that the mutation can be moved by P1 transduction. FIG. 2B shows the movement of the desired mutation into the galE::pTHE001 background using P1 transduction selecting for abR to generate an isogenic back-crossed mutant. FIG. 2C shows a second P1 transduction into the back crossed strain followed by selecting for growth on galactose minimal plates. Abbreviations: x=gene of interest, abR=antibiotic resistance gene, tetR=tetracycline resistance gene.

DEFINITIONS

To facilitate an understanding of the present invention, a number of terms and phrases are defined below:

As used herein, the terms "purified" and "isolated" refer to molecules (polynucleotides or polypeptides) or organisms that are removed or separated from their natural environment. "Substantially purified" molecules or organisms are at least 50% free, preferably at least 75% free, more preferably at least 90% and most preferably at least 95% free from other components with which they are naturally associated.

The term "wild-type" refers to a gene, gene product or organism that has the characteristics of that gene, gene product or organism when isolated from a naturally occurring source. A wild type gene or organism is that which is most frequently observed in a population and is thus arbitrarily designated the "normal" or "wild-type" form of the gene or organism.

In contrast, the terms "modified," "mutant," and "variant" refer to a gene, gene product or organism that displays modifications in sequence and or functional properties (i.e., altered characteristics) when compared to the wild-type gene, gene product or organism. It is noted that naturally occurring mutants can be isolated; these are identified by the fact that they have altered characteristics when compared to the wild-type gene, gene product or organism.

The term "antibody" refers to polyclonal and monoclonal antibodies. Polyclonal antibodies which are formed in the animal as the result of an immunological reaction against a protein of interest or a fragment thereof, can then be readily isolated from the blood using well-known methods and purified by column chromatography, for example. Monoclonal antibodies can also be prepared using known methods (See, e.g., Winter and Milstein, Nature, 349, 293-299, 1991). As used herein, the term "antibody" encompasses recombinantly prepared, and modified antibodies and antigen-binding fragments thereof, such as chimeric antibodies, humanized antibodies, multifunctional antibodies, bispecific or oligo-specific antibodies, single-stranded antibodies and F(ab) or $F(ab)_2$ fragments. The term "reactive" in used in reference to an antibody indicates that the antibody is capable of binding an antigen of interest. For example, an EHEC-reactive antibody is an antibody that binds to EHEC.

As used herein, the term "immune response" refers to the reactivity of a subject's immune system in response to an antigen. In mammals, this may involve antibody production, induction of cell-mediated immunity, and/or complement activation. In preferred embodiments, the term immune response encompasses but is not limited to one or more of a "lymphocyte proliferative response," a "cytokine response," and an "antibody response."

In particularly preferred embodiments, the immune response is largely reactive with EHEC cells. For instance, when used in reference to administration of EHEC gal mutants to a subject, the term refers to the immune response produced in the subject that reacts with the EHEC cells. Immune responses reactive with EHEC cells are measured in vitro using various methods disclosed herein.

The term "reactive with an antigen of interest" when made in reference to an immune response refers to an increased level of the immune response to the antigen of interest (e.g., EHEC) as compared to the level of the immune response to a control (e.g., irrelevant antigen).

The term "lymphocyte proliferative response" refers to EHEC-induced increase in lymphocyte numbers. Alternatively, or in addition, the term "proliferation" refers to the physiological and morphological progression of changes that cells undergo when dividing, for instance including DNA replication as measured by tritiated thymidine incorporation.

The term "cytokine response" refers to EHEC-induced cytokine secretion by lymphocytes as measured for instance by assaying culture supernatants for cytokine content (e.g., IL-2, IFNγ, TNFα, IL-4, etc) by ELISA.

The term "antibody response" refers to the production of antibodies (e.g., IgM, IgA, IgG) that bind to an antigen of interest (e.g., EHEC cells), this response is measured for instance by assaying sera by EHEC ELISA.

The term "adjuvant" as used herein refers to any compound that when injected together with an antigen, non-specifically enhances the immune response to that antigen. Exemplary adjuvants include but are not limited to incomplete Freunds adjuvant (IFA), aluminum-based adjuvants (e.g., AlOH, AlPO4, etc), and Montanide ISA 720.

The terms "excipient," "carrier" and "vehicle" as used herein refer to usually inactive accessory substances into which a pharmaceutical substance (e.g., EHEC cells) is suspended. Exemplary carriers include liquid carriers (such as water, saline, culture medium, aqueous dextrose, and glycols) and solid carriers (such as carbohydrates exemplified by starch, glucose, lactose, sucrose, and dextrans, anti-oxidants exemplified by ascorbic acid and glutathione, and hydrolyzed proteins).

The terms "mammals" and "mammalian" refer to animals of the class mammalian that nourish their young by fluid secreted from mammary glands of the mother, including human beings. The class "mammalian" includes placental animals, marsupial animals, and monotrematal animals.

The term "ruminant" as used herein refers to animals of the suborder Ruminantia or any other animal that chews a cud. In preferred embodiments, the term ruminant encompasses cattle, goats, sheep, bison, buffalo, deer, and antelope.

The term "bovine subject" as used herein refers to animals belonging to the genus *Bos*. In preferred embodiments, the term bovine encompasses cattle.

The term "control" refers to subjects or samples that provide a basis for comparison for experimental subjects or samples. For instance, the use of control subjects or samples permits determinations to be made regarding the efficacy of experimental procedures. In some embodiments, the term "control subject" refers to animals or cells receiving a mock treatment (e.g., adjuvant alone).

As used herein the terms "GalE" and "UDP-galactose-4-epimerase" refer to an enzyme (EC 5.1.3.2) that catalyzes the interconversion of UDP-glucose to UDP-galactose and the interconversion of UDP-N-acetylglucosamine to UDP-N-acetylgalactosamine. In an exemplary embodiment the term GalU refers to an *E. coli* O157:H7 enzyme having an amino acid sequence as set forth in GENBANK Accession No. NP_286480, herein incorporated by reference, encoded by a nucleic acid sequence complementary to residues 876559 to 877575 of GENBANK Accession No. NC_002655.2 herein incorporated by reference.

As used herein the terms "GalT" and "galactose-1-phophate uridylyltransferase" refer to an enzyme (EC 2.7.7.12) that catalyzes the interconversion of galactose-1-phosphate and glucose-1-phosphate via transfer of uridine monophosphate. In an exemplary embodiment the term GalT refers to an *E. coli* O157:H7 enzyme having an amino acid sequence as set forth in GENBANK Accession No. NP_286479, herein incorporated by reference, encoded by a nucleic acid sequence complementary to residues 875503 to 876549 of GENBANK Accession No. NC_002655.2 herein incorporated by reference.

As used herein the terms "GalK" and "galactokinase" refer to an enzyme (EC 2.7.1.6) that catalyzes the phosphorylation of galactose to galactose-1-phosphate as the first step in galactose metabolism. In an exemplary embodiment the term GalK refers to an *E. coli* O157:H7 enzyme having an amino acid sequence as set forth in GENBANK Accession No. NP_286478, herein incorporated by reference, encoded by a nucleic acid sequence complementary to residues 874351 to 875499 of GENBANK Accession No. NC_002655.2 herein incorporated by reference.

As used herein the terms "GalU," "glucose-1-phosphate uridylyltransferase" and UGP refer to an enzyme (EC 2.7.7.9) that catalyzes the transfer of a glucose moiety from glucose-1-phosphate to MgUTP, forming UDP-glucose and MgPPi. In an exemplary embodiment the term GalU refers to an *E. coli* O157:H7 enzyme having an amino acid sequence as set forth in GENBANK Accession No. NP_287481, herein incorporated by reference, encoded by a nucleic acid sequence as set forth in residues 1828438 to 1829346 of GENBANK Accession No. NC_002655.2 herein incorporated by reference.

As used herein the terms "shiga toxin 1 subunit A," "Stx1A" and "shiga-like toxin 1 subunit A" refers to the A subunit of an A-B type toxin that inhibits protein synthesis in eukaryotic cells and is thought to be required for the severe clinical manifestations of EHEC infection, such as hemorrhagic colitis and HUS (Karmali, *Clin Microbiol Rev,* 2:15-38, 1989). In an exemplary embodiment the term Stx1A refers to an *E. coli* O157:H7 protein having an amino acid sequence as set forth in GENBANK Accession No. NP_288673, herein incorporated by reference, encoded by a nucleic acid sequence complementary to residues 2996033 to 2996980 of GENBANK Accession No. NC_002655.2 herein incorporated by reference.

As used herein the terms "shiga toxin 2 subunit A," "Stx2A" and "shiga-like toxin 2 subunit A" refers to the A subunit of an A-B type toxin that inhibits protein synthesis in eukaryotic cells and is thought to be required for the severe clinical manifestations of EHEC infection, such as hemorrhagic colitis and HUS (Karmali, *Clin Microbiol Rev,* 2:15-38, 1989). In an exemplary embodiment the term Stx2A refers to an *E. coli* O157:H7 protein having an amino acid sequence as set forth in GENBANK Accession No. NP 286976, herein incorporated by reference, encoded by a nucleic acid sequence as set forth in residues 1352290 to 1353249 of GENBANK Accession No. NC_002655.2 herein incorporated by reference.

BRIEF DESCRIPTION OF THE INVENTION

Enterohemorrhagic *Escherichia coli* (EHEC), especially *E. coli* O157:H7 is an emerging cause of food-borne illness. Prior to development of the present invention, *E. coli* O157 could not be genetically manipulated using the generalized transducing phage P1, presumably because its O-antigen obscures the P1 receptor, the lipopolysaccharide (LPS) core subunit. The GalE, GalT, GalK and GalU proteins are necessary for modifying galactose before it can be assembled into the repeating subunit of the O-antigen. As disclosed herein *E. coli* O157:H7 gal mutants were constructed having little or no O-antigen. These strains were able to adsorb P1. P1 lysates grown on the gal strains could be used to move chromosomal markers between EHEC strains, thereby facilitating genetic manipulation of *E. coli* O157:H7. The gal mutants could easily be reverted to a wild type Gal+ strain using P1 transduction. The O157:H7 galETKM::aad-7 deletion strain was 500-fold less able to colonize the infant rabbit intestine compared to the isogenic Gal+ parent, although it displayed essentially no growth defect in vitro. Furthermore, a Gal+ revertant of this mutant out-competed the galETKM deletion strain to a similar extent as wild type indicating that the O157 O-antigen is an important intestinal colonization factor. Compared to the wild type, EHEC gal mutants were 100-fold more sensitive to a peptide derived from bactericidal/permeability-increasing protein (BPI), a bactericidal protein found on the surface of intestinal epithelial cells. Thus, the EHEC gal mutants are sensitive to host-derived anti-microbial polypeptides.

DETAILED DESCRIPTION OF THE INVENTION

I. O-Antigen Mutants of EHEC

Lipopolysaccharide (LPS), found in the outer membrane of gram-negative bacteria, is composed of lipid A, core oligosaccharide and repeating O-antigen subunits. The O-antigen is covalently linked to the outer region of the core oligosaccharide, and it appears to act as a barrier that can protect enteric pathogens against toxic agents encountered in host gastrointestinal (GI) tracts (Peschel, *Trends Microbiol,* 10:179-186, 2002). For example, in *Vibrio cholerae,* galU and galE mutants lacking O-antigen are defective in intestinal colonization although they have no growth defect in rich medium. These mutants were more sensitive than O-antigen-producing strains to killing by complement and cationic antimicrobial peptides, suggesting that their defect in colonization is attributable to their sensitivity to bactericidal substances elaborated by the host GI tract (Nesper et al., *Infect Immun,* 69:435-445, 2001).

Like many enteric pathogens, *E. coli* O157 produces LPS that contains an extensive O-antigen. The O157 O-antigen subunit consists of N-acetyl-D-perosamine, L-fucose, D-glucose, and N-acetyl-D-galactose (Perry et al., *Biochem Cell Biol,* 64:21-28, 1986). Production of N-acetyl-D-galactose requires its precursor, galactose, be modified by the enzymes GalE, GalT, GalK and GalU. *Salmonella enterica serovar Typhimurium* (*S. Typhimurium*) and *E. coli* gal mutants no longer make O-antigen (Genevaux et al., *Arch Micrbiol,* 172: 1-8, 1999; Ornellas et al., *Virol,* 60:491-502, 1974; and Raetz, "Bacterial lipopolysaccharides: a remarkable family of bioactive macroamphilies," in Neidhardt (ed.), *Escherichia coli and Salmonella,* vol. 1, ASM Press, pp 1035-1063, 1996). The inner region of the LPS core oligosaccharide, which is conserved in many enterics, serves as the receptor for bacteriophage P1. Phage P1 has been a workhorse for genetic manipulation of *E. coli* K-12 for many decades. P1-mediated generalized transduction enables movement of mutations for generation of isogenic bacterial strains, which is often required for proving the linkage between particular genotypes and phenotypes. In *S. Typhimurium,* which has a LPS core oligosaccharide similar to that of *E. coli* K-12, the long O-antigen obscures the core oligosaccharide and prevents P1 from adsorbing to the bacteria. O-antigen mutants (ΔgaI, ΔgalE, and ΔgalU) of *S. Typhimurium* have been shown to be P1-sensitive (Ornellas et al., *Virol,* 60:491-502, 1974).

II. P1-Mediated Generalized Transduction of EHEC O-Antigen Mutants

Generalized transduction of EHEC by P1 has not been previously described. As disclosed herein, O157:H7 gal mutants were produced, which are P1 sensitive and permit P1-mediated movement of genetic markers between EHEC strains. In contrast, wild type EHEC O157:H7 are resistant to P1. Additionally, the methods described herein allow for a simple reversion to convert P1 sensitive strains back to wild type P1 resistant strains.

The methods described herein are adaptable for use with other EHEC serotypes, as well as for other pathogenic *E. coli* such as enteropathogenic *E. coli* (EPEC), enterotoxigenic *E. coli* (ETEC), and uropathogenic *E. coli* (UPEC). An exemplary EPEC strain is UT189 (Mulvey et al., Infect Immun, 69:4572-4579, 2001). An exemplary ETEC strain is serotype O78:H11, LT+, ST+, strain H10407 (Evans et al., J Infect Dis, 136(S):S118-S123, 1977. An exemplary EPEC strain is 0127: H6 wild type strain E2348/69 (Jerre et al., Proc Natl Acad Sci USA, 87:7839-7843, 1990).

FIG. 2 outlines a general scheme for using P1 transduction in the genetic manipulation of EHEC. This figure describes methods for routinely generating isogenic EHEC strains. This ability to move chromosomal markers enables generation of isogenic strains containing single or multiple mutations. Given the relative ease of the P1 transduction technique outlined here, it is now possible to back cross mutations generated with the lambda red system into genetically identical backgrounds.

III. Colonization Defect of EHEC O-Antigen Mutants

Interestingly, P1-sensitive, galETKM O157:H7 mutant was extremely attenuated in its ability to colonize the infant rabbit intestine. Thus during development of the present invention, the O157 O-antigen was found to be an important EHEC colonization factor. Tissue culture experiments indicate that the O157 O-antigen is not likely to be involved in EHEC adherence to intestinal epithelial cells and may reduce EHEC type 3 secretion of effectors that promote adherence (Bilge et al., *Infect Immun,* 64:4795-4801, 1996; Cockerill et al., *Infect Immun,* 64:3196-3200, 1996; and Paton et al., *Microbial Pathogenesis,* 24:57-63, 1998). The sensitivity of the O157 gal mutants to BPI indicates that at least part of the colonization defect of the galETKM mutant is due to its reduced resistance to host anti-microbial factors. Nonetheless, knowledge of mechanism is not required in order to make and use the present invention.

Although O157 strains are most commonly associated with EHEC-related illness in North America, Europe and Japan, other EHEC serotypes (O26, O91, O103, and O111) can also cause significant human disease (Paton et al., *Clin Microbiol Rev,* 11:450-479, 1998). It is contemplated that O-antigens from different EHEC serotypes vary in resistance to host killing and therefore vary in intestinal colonization capacity as has been seen in K1 *E. coli* (Pluschke et al., *Infect Immun,* 43:684-692, 1998). The P1 transduction method outlined herein should facilitate the construction of isogenic strains differing only in their O-antigens, thus enabling a more extensive exploration of the role of particular O-antigens in EHEC virulence.

O-antigens are contemplated to act as important barriers against extracellular assaults mounted by the host immune system. O-antigen mutants of enterics like *V. cholerae, Klebsiella* serotype O1:K20, and *Shigella flexneri* are more susceptible to anti-microbial peptides and complement killing (McCallum et al., *Infect Immun,* 57:3816-3822, 1989; Nesper et al., *Infect Immun,* 69:435-445, 2001; and West et al., *Science,* 307:1313-1317, 2005). Additionally, *S. Typhi, Brucella melitensis* and *V. cholerae* O-antigen mutants have been shown to be impaired in intestinal colonization (Chiang et al., *Infect Immun,* 67:976-980, 1999; Gilman et al., *J Infect Dis,* 136:717-723, 1997; Nesper et al., *Infect Immun,* 69:435-445, 2001; and Rajashekara et al., *Infect Immun,* 74:2925-2936, 2006). In fact, the only oral live-attenuated vaccine against *Salmonella enterica serovar Typhi* used in the United States is a galE mutant. Given the pronounced attenuation of the O157: H7 ΔgalETKM::aad-7 mutant, EHEC gal mutants are contemplated to be clinically and agriculturally useful vaccines.

IV. Utilities

In some embodiments, the present invention further provides *E. coli* bacterium comprising an inactivating mutation in one or more galactose-modifying enzymes, as well as an inactivating mutation in one or both of a shiga toxin A subunit and a shiga toxin B subunit. Thus the present invention provides live attenuated bacteria having defects in intestinal colonization and which are relatively nonpathogenic for use as vaccines and delivery vehicles for genes and gene products and to methods for their preparation. In some preferred embodiments, the present invention provides E. coli O157:H7 gal stx mutants and methods for their production and use.

In particular the present invention provides methods for producing an attenuated bacterium comprising (a) introducing one or more inactivating mutations in a galactose-modifying enzyme; and (b) introducing one or more inactivating mutations in a shiga toxin, wherein steps (a) and (b) may be performed in any order. Furthermore the present invention provides methods for inducing an immune response comprising administering immunogenic compositions or vaccines comprising live or killed E. coli bacterium comprising an inactivating mutation in one or more galactose-modifying enzymes, as well as an inactivating mutation in one or both of a shiga toxin A subunit and a shiga toxin B subunit to a subject under conditions suitable for inducing an immune response reactive with the E. coli bacterium.

Although live attenuated vaccines based on *Salmonella* mutants have shown promise in stimulating humoral, cell-mediated and mucosal immune responses to heterologous antigens (Calhoun et al., J Micrbiol Immunol Infect, 39:92-97, 2006), *Salmonella* species do not encode an intact type II secretion system. Many pathogens secrete important virulence factors via a type II secretion system (Sandkvist, Infect Immun, 69:3523-3535, 2001; and Dorsey et al., Cell Microbiol, 8:1516-1527, 2006), including cholera toxin from *Vibrio cholerae*, the heat-labile toxin from enterotoxigenic *E. coli* and Exotoxin A of *Pseudomonas aeruginosa*. Since EHEC synthesizes a functional type II secretion system, a live oral vaccine derived from EHEC may be made to secrete harmless components of these toxins. Such a vaccine is contemplated to induce an immune response that neutralizes the damaging effects of intact toxins.

The present invention also provides methods for producing an attenuated carrier bacterium for delivery of a desired gene product to a host, comprising (a) introducing one or more inactivating mutations in a galactose-modifying enzyme; (b) introducing one or more inactivating mutations in a shiga toxin; and (c) introducing a recombinant gene encoding the desired gene product to a bacterium, wherein steps (a), (b), or (c) may be performed in any order.

Furthermore the present invention provides methods for inducing an immune response comprising administering immunogenic compositions or vaccines comprising live or killed E. coli bacterium comprising an inactivating mutation in one or more galactose-modifying enzymes, as well as an inactivating mutation in one or both of a shiga toxin A subunit and a shiga toxin B subunit, and a gene encoding a heterologous antigen, to a subject under conditions suitable for inducing an immune response reactive with the heterologous antigen.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µM (micrometers); nm (nanometers); (degrees Centigrade); U (units), mU (milliunits); min. (minutes); sec. (seconds); % (percent); kb (kilobase); bp (base pair); PCR (polymerase chain reaction); BPI (bactericidal/permeability-increasing protein); EHEC (enterohemorrhagic); LPS (lipopolysaccharide).

Example 1

Production of Enterohemorrhagic *E. coli* O157:H7 gal Mutants

This example describes the construction of O-antigen deficient *E. coli* O157:H7 mutants. As described herein, the EHEC mutants produced during development of the present invention are able to adsorb the generalized transducing phage P1 and do not display growth defects in vitro. However, the EHEC mutants poorly colonize the intestine in vivo and are sensitive to bactericidal/permeability-increasing protein (BPI).

Bacterial Strains and Growth. A list of strains used in during development of the exemplary EHEC mutants are shown in Table 1. Unless otherwise noted, strains were grown in LB broth or on LB agar plates. For antibiotic selection, agar plates were supplemented with ampicillin (80 µg/ml), spectinomycin (100 µg/ml) or tetracycline (6 µg/ml). MacConkey plates with 1% galactose or M63 (22 mM $KH_2PO_4$, 40 mM $K_2HPO_4$, 15 mM $(NH_4)_2SO_4$, 0.5 mg/liter $FeSO_4$) agar plates supplemented with 0.2% galactose and 0.1% casamino acids were used to test whether a strain could metabolize galactose.

To generate the deletion-insertion mutations in the gal genes, a one-step gene inactivation method adapted from Datsenko and Wanner (*Proc Natl Acad Sci USA*, 97:6640-6645, 2000) was used. In this method, a temperature-sensitive plasmid (pKD46) encoding lambda red recombinase was transformed into EDL933. To make the ΔgalU::aad-7 mutant TEA023 and the ΔgalETKM::aad-7 mutant TEA026, the spectinomycin resistance gene (aad7) was amplified from the pVi36 plasmid (provided by V. Burrus, University of Sherbrooke) template using primers TE139 (5'-ATGGCTGCCA TTAATACGAA AGTCAAAAAA GCC set forth as SEQ ID NO:1) and TE140 (5'-TTACTTCTTA ATGCCCATCT CTTCTTCAAG CCA set forth as SEQ ID NO:2) or TE137 (5'-ATGCTATGGT TATTTCATAC CATAAGCCTA ATGGAGCCCG GCGGATTTGT CCTACTC set forth as SEQ ID NO:3) and TE138 (5'-TTACTCAGCA ATAAACTGAT ATTCCGTCAG GCTCTAAGCA CTTGTCTCCT GTTTA set forth as SEQ ID NO:4) respectively. For the ΔgalETKM::tetA mutant TEA028, the tetracycline resistance gene (tetA) was amplified from the pAH162 plasmid (Haldimann et al., *J Bacteriol*, 183:6384-6393, 2001) template using TE141 (5'-ATGCTATGGT TATTTCATAC CATAAGCCTA ATGGAG-GATG CCTGGCAGTT CCCTACTC set forth as SEQ ID NO:5) and TE142 (5'-TTACTCAGCA ATAAACTGAT ATTCCGTCAG GCTTTAGGTG GCGGTACTTG GGTCGA set forth as SEQ ID NO:6). After electroporation of the PCR products, cells were incubated in SOB 0.2% L-arabinose for 2 hours then plated on selective media at 37° C. For the ΔgalU::aad-7 mutation, the spectinomycin resistance gene replaced all of the galU gene except for the first 33 bp and the last 30 bp of the galU open reading frame. For the ΔgalETKM::aad-7 and ΔgalETKM::tetA mutations, the antibiotic resistance gene replaced all of the galETKM operon except for the first 36 bp of the galE gene and the last 30 bp of the galM gene. The pTHE001 plasmid was constructed to generate an insertion mutation in galE. First, a 460 bp internal fragment of the galE gene was amplified by PCR using primers TE013 (5'-GCAAGGATCC GACGTTTGTT GAAGGC-GATA set forth as SEQ ID NO:7) and TE014 (5'-GGCAT-AAGGG AATTCGGAAT GCCTTGCGGA set forth as SEQ ID NO:8). This PCR product was digested with BamHI and then cloned into the BglII site of the conditional plasmid pGP704 (Miller et al., *J Bacteriol*, 170:2575-2583, 1988). The resulting pTHE001 plasmid was mobilized using the RP4+ helper strain WM3064 (provided by W. Metcalf, University of Illinois, Urbana-Champaign) into EDL933. To generate the Gal+ revertant TEA040, the galE::pTHE001 mutation was moved from TEA007 into the galETKM::aad-7 strain (TEA026) by P1 transduction, selecting for ampicillin resistance. The resulting strain was then used as a recipient for P1 transduction of the galETKM+ allele from TEA023. Gal+ transductants were selected on M63 agar plates supplemented with 0.2% galactose and 0.1% casamino acids.

13,000 rpm for 1 minute, diluted in phosphate-buffered saline (PBS) and spotted on top agar lawns of MC4100 for titering. Lysates were stored at 4° C. in the dark with 0.5 ml chloroform.

P1 Transduction. Overnight cultures (0.5 ml) of recipient bacteria grown in LB were pelleted and resuspended in 100 µl MC (5 mM $MgSO_4$ 50 mM $CaCl_2$). About 50 µl of P1 lysate was added to the cells, which were then incubated at 37° C. for 15-30 minutes. LB with 10 mM sodium citrate (0.5-1 ml) was added to each tube and incubated for 1 hour at room temperature. Each tube was centrifuged at 6,000 rpm for 2 minutes, resuspended in 100 µl 1M sodium citrate and plated on selective media.

TABLE 1

List of Strains

| Strains | Genotype/Description | Source* |
|---|---|---|
| EDL933 | O157:H7 | Perna et al. |
| TEA007 | EDL933 galE::pTHE001 | this study |
| TEA023 | EDL 933 ΔgalU::aad-7 | this study |
| TEA026 | EDL 933 ΔgalETKM::aad-7 | this study |
| TEA028 | EDL 933 ΔgalETKM::tetA | this study |
| TEA040 | EDL933; Gal+ revertant of TEA026 | this study |
| CAG5051 | HfrH nadA57::Tn10 thi-1 relA1 spoT supQ80 | Singer et al. |
| MC4100 | araD139 Δ(arg-lac)U169 rpsL150 relA1 flbB5301 fruA25 deoC1 ptsF25 | laboratory stock |
| EDL933/ pKD46 | (oriR101 bla Para-λ gam bet exo) | this study |
| BW19851/ pGP704 | RP-4-2-Tc::Mu-1 kan::Tn7 integrant creB150 hsdR17 endA zbf-5 uidA(ΔMlu1)::pir(wt) recA1 thi/pGP704 (oriR6K mobRP4 $Ap^R$) | Miller et al. |
| WM3064/ pTHE001 | thrB1004 pro thi rpsL hsdS lacZΔM15 RP4-1360 Δ(araBAD)567 ΔdapA1341::[erm pir(wt)]/pTHE001 (oriR6K mobRP4 $Ap^R$ 'galEEDL933') | this study |
| DH5αλpir+/ pVi36 | endA1 hadR17 thi-1 recA1 Δ(lacIZYA-argF)U169 deoR (p80 lacZΔM15) gyrA relA1/pVi36 (oriR6K aad-7) | Burrus |
| BW23473/ pAH162 | Δ(lacIZYA-argF)U169 rph-1 rpoS396(Am) robA1 creC510 hsdR514 DendA9 5 uidA(ΔMlu1)::pir(wt) recA1/pAH162 (tetA) | Haldimann et al. |

*Sources include Perna et al., Nature, 409: 529-533, 2001; Singer et al., Microbiol Mol Biol Rev, 53: 1-24, 1989; Miller et al., J Bacteriol, 170: 2575-2583, 1988; and Haldimann et al., J Bacteriol, 183: 6384-6393, 2001.

P1 Adsorption and Sensitivity Assays. P1 adsorption assays were performed using a P1 lysate grown on the *E. coli* K-12 strain MC4100. Approximately 100 µl of overnight culture was pelleted by centrifugation and resuspended in 100 µl of LB broth. 100 µl of the P1 lysate was then added to these cells. After 15 minutes of incubation at 37° C., cells were pelleted by centrifugation at 6,000 rpm in an Eppendorf centrifuge at 4° C. for 2 minutes. The P1 titers of the supernatants were then determined by plaquing using MC4100 as an indicator strain. To plaque P1, phage lysates were spotted on top agar (LB containing 2 mM $MgSO_4$ and 10 mM $CaCl_2$ and 0.7% agar) lawns of MC4100.

To test for sensitivity of strains to P1 lysis each strain was cross-streaked against P1. A single line of P1 (100 µl; ~$10^9$ pfu/ml) was allowed to dry on a LB agar plate. For each bacterial strain, a single streak was then drawn across the perpendicular line of phage P1. Strains resistant to P1 grow on both sides of the line of P1, while susceptible strains partially lyse following an encounter with P1.

P1 Lysate Production. P1 lysates of various EHEC strains were generated by growing 1:100 dilution overnight cultures of each strain in 2.5 ml of LB containing 2 mM $MgSO_4$ and 10 mM $CaCl_2$ and incubating for 1 hour at 37° C. with agitation. Then, 100 µl of a P1 lysate grown on MC4100 was added to each culture. After 2-3 hours of incubation at 37° C. with agitation, lysis of the cultures was observed. Tubes were transferred to ice and any remaining intact bacteria were lysed with 0.5 ml chloroform. Lysates were then centrifuged at In Vitro Competition Assays. A 1:1 mixture of mutant (TEA026) and wild type (EDL933 or TEA040) initially containing ($5 \times 10^7$) bacteria/ml was incubated in LB broth at 37° C. with agitation overnight. Each assay was then diluted and plated on LB agar. After overnight growth, bacteria were replica plated on selective media to determine the number of mutant and wild type bacteria. Each assay was performed at least three times.

Competition Assays in Infant Rabbits. The infant rabbit model was used to test the colonization ability of EHEC strains (Ritchie et al., *Infect Immun*, 71:7129-7139, 2003). Three-day old New Zealand white rabbits were orally inoculated with a 1:1 mixture of TEA026 and wild type (EDL933 or TEA040) containing $2.5 \times 10^8$ total bacteria, which were washed one time and resuspended in PBS. Seven days after inoculation, rabbits were sacrificed and their gastrointestinal tracts removed. Portions of the ileum, mid-colon and cecum were then homogenized, diluted and plated on sorbitol-MacConkey agar. After overnight growth, bacteria were replica plated on LB agar containing spectinomycin (100 µg/ml) to determine the number of TEA026 bacteria.

BPI Sensitivity Assays. The BPI-derived peptide P2 (SKISGKWKAQKRFLKMSGNFGC, set forth as SEQ ID NO:9), which retains the anti-bacterial activity of whole protein (Gray et al., *Infect Immun*, 62:2732-2739, 1994; and Little et al., *J Biol Chem*, 269:1865-1872, 1994), was used to assess EHEC sensitivity. For these assays, bacteria grown overnight in LB were washed once in PBS and resuspended in PBS pH 6.2. Then 5×10$^7$ bacteria with or without 30 μg P2 (Tufts University Core Facility) were incubated in 0.5 ml PBS pH 6.2 for 45 minutes at 37° C. After incubation, assays were placed on ice, diluted and plated on LB. Each assay was performed in triplicate and repeated in three independent experiments.

O157:H7 gal mutants can adsorb P1 and are sensitive to P1 lysis. In many enteric bacteria, extensive LPS O-antigens obscure the LPS core oligosaccharide and thereby prevent adsorption of and lysis by phage P1. Synthesis of the O157:H7 O-antigen requires modification of galactose by the galF, galT, galK and galU gene products. As described herein phage infection of and adsorption by the sequenced O157:H7 isolate EDL933 was compared to that of four gal derivatives: the deletion mutants ΔgalETKM::aad-7 (TEA026), ΔgalETKM::tetA (TEA028) and ΔgalU::aad7 (TEA023) and the insertion mutant ΔgalE::pTHE001 (TEA007).

To assess whether gal loci influence infection of EHEC by phage P1, cross streak experiments were performed. A streak of each bacterial strain was drawn across a perpendicular line of P1, and the consequences of encountering phage were assessed. There was no change in the growth of wild type EDL933 in response to P1, indicating that this strain is resistant to phage infection. In contrast, all four gal mutants were lysed by phage P1.

To explore why the gal mutants are more susceptible to P1 infection, adsorption of P1 by the mutants was tested. Phage adsorption to the host bacterium is an essential first step in phage infection. In these assays, each gal mutant was incubated with P1 and then centrifuged to pellet any phage adsorbed to the bacteria. Supernatants were then assayed to determine the number of unadsorbed P1. As shown in Table 2, the wild type strain adsorbed ~40% of the phage, suggesting that there may be some nonspecific interactions between EHEC and P1, since the wild type strain is resistant to P1 infection and therefore presumed to have inaccessible core oligosaccharide. However, all four gal mutants adsorbed ~95% of the P1. Access to P1's receptor is contemplated to be less impeded in the mutant strains than it is in the wild type strain. Nonetheless, knowledge of the mechanism is not required in order to make and use the present invention.

TABLE 2

P1 Adsorption and P2 Sensitivity of EHEC strains

| Strain | % Adsorbed P1[1] | % Survival after P2 challenge[2] |
|---|---|---|
| EDL933 (wild type) | 27.4 | 38 |
| TEA007 (galE::pTHE001) | 93.5 | 0.054 |
| TEA023 (ΔgalU::aad-7) | 96.6 | 0.29 |
| TEA026 (ΔgalETKM::aad-7) | 95.2 | 0.014 |
| TEA028 (ΔgalETKM::tetA) | 98.4 | 0.35 |
| TEA040 (Gal+ revertant) | 15.6 | 32 |

[1]% Adsorbed P1 = the number of P1 plaques obtained after incubation with bacteria/the number of P1 plaques obtained after incubation without bacteria × 100%. Each experiment was performed in triplicate and the means are shown. The p-value for each of the gal mutants versus wild type was less than 0.006. The p-value for TEA040 versus wild type was 0.65.
[2]% Survival after P2 challenge = the number of bacteria after incubation with P2/the number of bacteria after incubation without P2. Each experiment was performed in triplicate and the means are shown. The p-value for each of the gal mutants versus the wild type was less than 0.03. The p-value for TEA040 versus the wild type was 0.10.

Antibiotic resistance markers can be transduced between EHEC O157:H7 gal mutants by P1. The EHEC gal mutants were tested to determine whether they could serve as recipients or donors in P1 transduction. As expected, a nadA::Tn10 marker from an E. coli K-12 strain (CAG5051) could not be transduced into the wild type EDL933 strain by P1. In contrast, this marker could be transduced into the ΔgalU::aad-7 (TEA023), ΔgalETKM::aad-7 (TEA026), and the galE::pTHE001 (TEA007) strains.

Next to determine whether chromosomal markers could be transduced from the EHEC gal mutants, each of the mutants was used to generate a P1 lysate. The ΔgalU::aad-7, ΔgalETKM::aad-7 and galE::pTHE001 mutations could readily be transferred into the O157:H7 ΔgalETKM::tetA strain or into the E. coli K-12 strain MC4100. For each of these EHEC P1 transduction experiments, between 10-100 transductants were obtained. Thus as demonstrated herein, O157:H7 gal mutants are capable of being transduced by P1 and can be used to generate P1 lysates. However, the frequencies of transduction between the O157:H7 gal strains were ~100-fold lower than the frequency of P1 transduction between K-12 strains. The lower O157:H7 transduction efficiency is contemplated to be due to the abundance of prophage genes in O157:H7 that may affect replication or production of P1. Nonetheless, knowledge of the mechanism is not required in order to make and use the present invention.

Reversion of the gal mutant using P1 transduction. Gal-strains were reverted back to Gal+ to study the Gal+ EHEC strains that have been engineered using P1. The ΔgalETKM::aad-7 mutant (TEA026) was not reverted by transducing the galETKM+ allele from TEA023, indicating that the frequency of transduction was too low to obtain a revertant. Therefore, a two-step reversion method was employed. First the galE::pTHE001 mutation from TEA007 was moved into the galETKM strain (TEA026). This strain was then used as a recipient for P1 transduction of the galETKM+ allele from a donor lysate grown on the ΔgalU strain (TEA023). Gal+ transductants were selected on agar plates made with M63 minimal media containing 0.2% galactose and 0.1% casamino acids, and verified as Gal+ on MacConkey 1% galactose agar. The frequency of this transduction was as efficient as transfer of other EHEC chromosomal markers. One Gal+ revertant strain (TEA040) was chosen to test for P1 sensitivity. Like the isogenic wild type strain, this Gal+ revertant had a reduced capacity to adsorb P1 phage compared to the gal mutants (Table 2), was resistant to P1 lysis in a P1 cross-streak experiment, and was not able to serve as a recipient for P1 transduction. Nonetheless, knowledge of the mechanism is not required in order to make and use the present invention.

Figure 1:
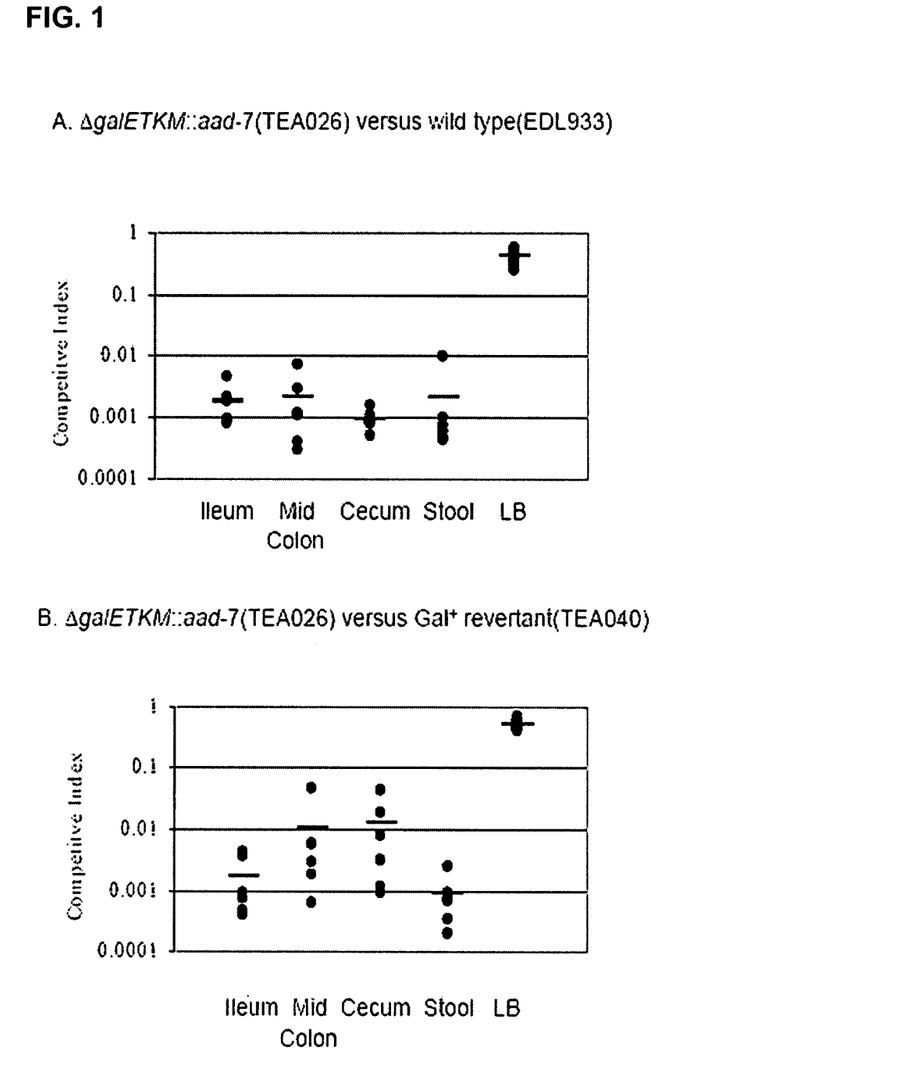
Figure 2:
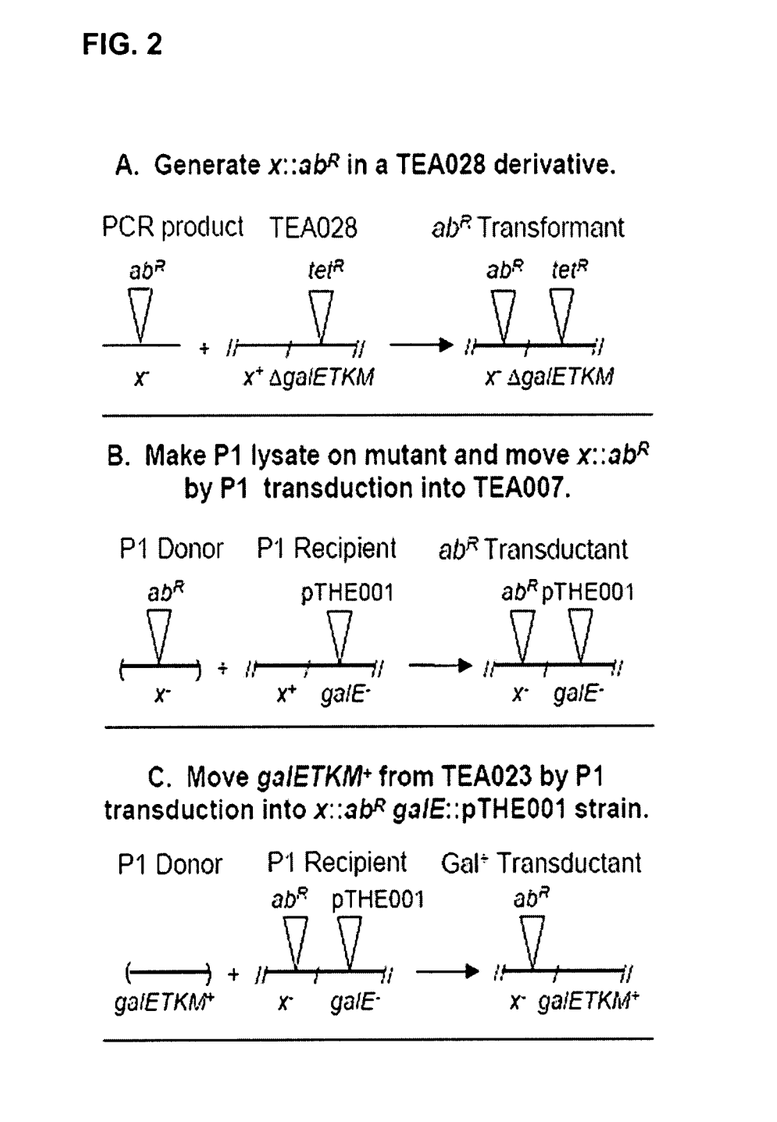

An O157:H7 galETKM mutant is dramatically impaired in colonization of the infant rabbit intestine. Previous studies have shown that galE mutants of S. enterica serovars are defective in intestinal colonization assays (Gilman et al., J Infect Dis, 136:717-723, 1977; and Hohmann et al., Infect Immun, 25:27-33, 1979). To determine whether the EHEC galETKM deletion had a similar defect in intestinal colonization, the galETKM:aad-7 deletion mutant (TEA026) was tested in a competition assay against the isogenic wild type strain (EDL933) using the EHEC-infant rabbit model. The galETKM deletion mutant (TEA026) was ~500-fold less able to colonize the infant rabbit ileum, cecum, and mid-colon (FIG. 1A). To demonstrate that this dramatic defect in intestinal colonization is due to the galETKM deletion, the Gal+ reverted strain was placed in competition against its ΔgalETKM::aad-7 parent strain. The Gal+ revertant (TEA040) out-competed the galETKM mutant (TEA023) to a similar extent as the wild type (FIG. 1B), demonstrating that the galETKM deletion accounts for the colonization defect of TEA026. In vitro competition assays where the galETKM strain and the wild type or the Gal+ revertant were grown in LB at 37° C. revealed that the galETKM mutation conferred a slight (~2-fold) but statistically significant growth defect in rich medium (FIG. 1). This minor in vitro growth defect cannot account for the drastic colonization defect of the gal mutant. Overall these findings indicate that the O157 O-antigen is critical for EHEC intestinal colonization. Nonetheless, knowledge of the mechanism is not required in order to make and use the present invention.

O157:H7 gal mutants are more sensitive to BPI killing. Host organisms often produce anti-microbial peptides, such as cryptidins, as effectors of innate immunity. Bactericidal/permeability-increasing protein (BPI) is a 55- to 60-kDa protein that is found in the blood and on surfaces of epithelial cells throughout the gastrointestinal tract (Canny et al., *Proc Natl Acad Sci USA,* 99:3902-3907, 2002). BPI binds the lipid A component of LPS and has potent bactericidal activity against gram-negative bacteria (Gazzano-Santoro et al., *Infect Immun,* 60:4754-4761, 1992). Given that O157 gal mutants likely lack O-antigen, it was contemplated that these mutants would be more sensitive to BPI than the wild type strain, since the lipid A portion of the gal strains' LPS would be more accessible to BPI binding. P2, a peptide that contains BPI residues 86 to 104 and which has the same cytotoxic activity as the entire protein was used to test whether the O157:H7 gal mutants have increased susceptibility to BPI. Bacteria were incubated in the presence or absence of P2 before enumerating the bacteria. Each of the gal mutants was far more sensitive to P2 than the wild type EHEC strain or the Gal+ revertant (Table 2). These data indicate that O157 O-antigen is important for EHEC resistance to BPI. Nonetheless, knowledge of the mechanism is not required in order to make and use the present invention.

Example 2

Production of *E. coli* O157:H7 gal stx2 Mutants

This example describes the construction of O-antigen deficient, shiga toxin 2 deficient *E. coli* O157:H7 mutants. The *E. coli* O157:H7 gal stx2 mutants are contemplated to poorly colonize the intestine in vivo, cause only mild diarrhea and result in reduced intestinal inflammation in comparison to isogenic *E. coli* O157:H7.

Bacterial Strain Construction. *E. coli* O157:H7 gal stx2 mutants are constructed using the PCR based "one-step gene inactivation system" adapted from Datsenko and Wanner (*Proc Nail Acad Sci USA,* 97:6640-6645, 2000). The pKD4 plasmid is used as a template to amplify a kanamycin resistance gene for these studies. PCR primers are designed using DNA sequences derived from *E. coli* O157:H7 reference strain EDL933 per a published report (Ritchie et al., *Infect Immun,* 71:7129-7139, 2003) and as follows: for $stx_{2AB}$, JRW1 (5'-ATGAAGTGTA TATTATTTAA ATGGGTACTG TGCCTGGTGT AGGCTGGAGC TGCTTCG-3' set forth as SEQ ID NO:10) and JRW2 (5'-TTATGCCTCA GTCATTATTA AACTGCACTT CAGCAACATA TGAATATCCT CCTTA-3' set forth as SEQ ID NO:11). PCR products were electroporated into TEA026 (ΔgalETKM::aad-7) and TEA028 (ΔgalETKM::tetA) previously transformed with the lambda Red-encoding plasmid pKD46, to make ΔgalETKM::aad-7/Δstx2ab::kan and ΔgalETKM::tetA/Δstx2ab::kan, respectively. Recombinants containing the kanamycin resistance gene in place of the gene of interest are selected on L-agar plates containing 50 μg/ml kanamycin, and the deletion of the gene of interest was confirmed by PCR analyses. The growth rates of new strains are not contemplated to differ from that of EDL933 during in vitro growth in LB at 37° C.

Animal protocols. Litters of 2-day-old New Zealand White rabbits are obtained from a commercial breeding company (Pine Acre Rabbitry, Norton, Mass.). Each litter is housed as a group and nursed by the mother. Three-day-old rabbits are intragastrically inoculated with *E. coli* mutant strains of interest or phosphate-buffered saline (PBS) using size 5 French catheters with flexible tips (Arrow International, Reading, Pa.). Bacterial doses of $5\times10^8$ CFU per 90 g of rabbit body weight are used in most experiments. For infant rabbit experiments, bacteria are grown overnight in LB at 37° C., harvested by centrifugation, and then resuspended in sterile PBS (pH 7.2) and adjusted to a cell density of about $10^9$ CFU/ml. Postinoculation, the infant rabbits are weighed daily and observed twice daily for clinical signs of illness. Diarrhea is scored as follows: none, no diarrhea (normal pellets are dark green, hard, and formed); mild, diarrhea consisting of a mix of soft yellow-green unformed and formed pellets, resulting in light staining of the hind legs; severe, diarrhea consisting of unformed or liquid stool, resulting in significant staining of the perineum and hind legs. In most experiments, rabbits are necropsied 7 days postinoculation. All rabbits were necropsied by intracardiac injection with 1 ml of saturated KCl solution following isoflurane anesthesia (Aerrane, Baxter, Deerfield, Ill.). At necropsy, the intestinal tract from the duodenum to the anus is removed and samples are obtained for histologic and microbiologic analyses. To limit any litter-specific effects, at least two different litters are used to test each type of inoculum studied.

Histology. Tissues are fixed in 10% neutral-buffered formalin, routinely processed for histology, and stained with hematoxylin and eosin (H&E). The samples are semi-quantitatively assessed for infiltration of heterophils, mononuclear cells, and edema or congestion by a comparative pathologist blinded to the sample identity. Sections are evaluated for heterophil inflammation using the following criteria: 0, none; 1, scattered individual cells or small clusters limited to the superficial lamina propria; 2, multifocal aggregates involving the entire mucosa surface with small numbers in the lumen; 3, coalescing heterophilic mucosal inflammation with abundant cell extrusion into the lumen; and 4, necrotizing inflammation with ulceration, large heterophilic intraluminal rafts, and extension into submucosal and deeper layers. Sections are evaluated for mononuclear cells (predominantly lymphocytes and plasmacytes) using the following criteria 0, normal; 1, slightly increased numbers in the lamina propria; 2, moderately increased numbers with mild separation of the crypts; 3, markedly increased mononuclear cells with decreased crypts and prominent intramucosal follicles; 4, effacing mononuclear cell inflammation with large mucosal and/or submucosal follicles ±extension into deeper layers. Edema, congestion, and hemorrhage are subjectively evaluated as follows: 0, none; 1, mild vascular congestion and/or edema limited to the lamina propria; 2, moderate, involving both mucosa and submucosa; 3, severe congestion and edema f small hemorrhages of mucosa and submucosa and edema of the serosa; and 4, severe diffuse transmural congestion, edema, and multifocal hemorrhage. Samples for transmission electron microscopy from the ceca and distal colons of rabbits necropsied 2 days postinoculation are fixed in 2.5% glutaraldehyde (pH 7.3) buffered in 0.1 M sodium cacodylate. Ultrathin sections of these samples are then stained with uranyl acetate and lead citrate, post fixed with osmium tetroxide, before examination on a Phillips CM-10 transmission electron microscope.

Example 3

Immunization with *E. coli* O157:H7 gal stx2 Mutants

This example describes the administration of O-antigen deficient, shiga toxin 2 deficient *E. coli* O157:H7 mutants to a subject under conditions suitable for induction of an *E. coli* O157:H7-reactive immune response. The methods described herein are adapted from US Publication No. 2002/0160020 of Finlay and Potter, herein incorporated by reference.

Experimental Animals. Cattle, between the ages of 8 and 12 months are purchased from local ranchers. Fecal samples are obtained daily from each animal for 14 days. The number of EHEC O157:H7 in the fecal samples is determined by plating on Rainbow Agar. The plates are incubated at 37° C. for 2 days and black colonies are enumerated. Growth is scored from 0-5. Animals having a score of 0 (no EHEC O157:H7) are used in all experiments.

Immunization. Sixteen cattle are divided in two groups of eight animals with group 1 receiving a composition comprising live *E. coli* O157:H7 gal stx2 mutants and group 2 receiving excipient alone by oral-gastric intubation on day O, Seroconversion is assayed using an enzyme-linked immunosorbent assay (ELISA) on days 0 (pre-immunization), 14, 21 and 28. Briefly, EHEC O157:H7 is used to coat the wells of microtiter plates overnight at 4° C. The wells are washed, and then blocked with 0.5% nonfat dried milk in PBS. Serial dilutions of sera are added to each well and incubated for 2 hr at 37° C. The wells are washed before incubation with a 1:5000 dilution of peroxidate-conjugated rabbit anti-bovine immunoglobulin M, G and A for 1 hr at 37° C. Cattle of group 1 are contemplated to develop high-titer anti-EHEC antibody responses.

Example 4

Challenge of *E. coli* O157:H7 gal stx2 Mutant-Immunized Subjects

This example describes the effects of immunizing a mammalian subject with O-antigen deficient shiga toxin 2 deficient *E. coli* O157:H7 mutants on intestinal colonization and fecal shedding of an EHEC challenge strain deficient in shiga toxin 2.

EHEC Challenge. At day 36, Group 1 and Group 2 animals of Example 3 are challenged with approximately $10^8$ CFU of EHEC O157:H7 by oral-gastric intubation. Fecal shedding is monitored for 14 days. Briefly, fecal material is weighed, suspended in sterile saline and inoculated into culture media. After overnight growth, bacteria are replica plated on LB agar containing spectinomycin (100 μg/ml) to determine the number of challenge bacteria. Fewer experimental animals are contemplated to shed EHEC O157:H7 than control animals. Moreover, experimental animals that shed EHEC O157:H7 are contemplated to do so for a shorter period of time than control animals. In addition the total number of EHEC O157:H7 bacteria isolated from fecal samples is contemplated to be significantly lower among the EHEC-vaccinated group as compared to the placebo group.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in molecular biology, genetics, microbiology, immunology or related fields are intended to be within the scope of the following claims.

What is claimed is:

1. A method of inducing an immune response specific to *E. coli* O157:H7 in a mammalian subject comprising administering a composition to said subject under conditions suitable for inducing an immune response, wherein the composition comprises an attenuated *E. coli* O157:H7 having an inactivating mutation in shiga toxin 2 subunit A (stx2A) and an inactivating mutation in one or more galactose-modifying enzymes that results in O-antigen deficiency and deficiency in intestinal colonizing capacity compared to wild-type parent *E. coli* O157:H7, wherein the composition further comprises an adjuvant or an excipient, thereby inducing the immune response in the mammalian subject.

2. The method of claim 1, wherein the one or more galactose-modifying enzymes are selected from the group consisting of GalE, GalU, GalT and GalK.

3. The method of claim 1, wherein the administering is by oral or intrarectal route.

4. The method of claim 1, wherein said mammalian subject is a ruminant.

5. The method of claim 4, wherein said ruminant is a bovine subject.

6. The method of claim 1, wherein the method induces an antibody response specific to *E. coli* O157:H7.

7. The method of claim 1, wherein the attenuated *E. coli* O157:H7 further comprises a gene encoding a heterologous antigen.

8. The method of claim 7, wherein the heterologous antigen is a protein.

9. The method of claim 8, wherein the protein is of a bacterial, viral or parasitic pathogen.

* * * * *

SEQUENCE LISTING

```
<160> NUMBER OF SEQ ID NOS: 11

<210> SEQ ID NO 1
<211> LENGTH: 33
<212> TYPE: DNA
<213> ORGANISM: Artificial Sequence
<220> FEATURE:
<223> OTHER INFORMATION: The nucleic acid was designed and synthesized.

<400> SEQUENCE: 1
atggctgcca ttaatacgaa agtcaaaaaa gcc                                   33

<210> SEQ ID NO 2
<211> LENGTH: 33
<212> TYPE: DNA
<213> ORGANISM: Artificial Sequence
<220> FEATURE:
<223> OTHER INFORMATION: The nucleic acid was designed and synthesized.

<400> SEQUENCE: 2
ttacttctta atgcccatct cttcttcaag cca                                   33

<210> SEQ ID NO 3
<211> LENGTH: 57
<212> TYPE: DNA
<213> ORGANISM: Artificial Sequence
<220> FEATURE:
<223> OTHER INFORMATION: The nucleic acid was designed and synthesized.

<400> SEQUENCE: 3
atgctatggt tatttcatac cataagccta atggagcccg gcggatttgt cctactc       57
```

```
<210> SEQ ID NO 4
<211> LENGTH: 55
<212> TYPE: DNA
<213> ORGANISM: Artificial Sequence
<220> FEATURE:
<223> OTHER INFORMATION: The nucleic acid was designed and synthesized.

<400> SEQUENCE: 4
ttactcagca ataaactgat attccgtcag gctctaagca cttgtctcct gttta         55

<210> SEQ ID NO 5
<211> LENGTH: 58
<212> TYPE: DNA
<213> ORGANISM: Artificial Sequence
<220> FEATURE:
<223> OTHER INFORMATION: The nucleic acid was designed and synthesized.

<400> SEQUENCE: 5
atgctatggt tatttcatac cataagccta atggaggatg cctggcagtt ccctactc      58

<210> SEQ ID NO 6
<211> LENGTH: 56
<212> TYPE: DNA
<213> ORGANISM: Artificial Sequence
<220> FEATURE:
<223> OTHER INFORMATION: The nucleic acid was designed and synthesized.

<400> SEQUENCE: 6
ttactcagca ataaactgat attccgtcag gctttaggtg gcggtacttg ggtcga        56

<210> SEQ ID NO 7
<211> LENGTH: 30
<212> TYPE: DNA
<213> ORGANISM: Artificial Sequence
<220> FEATURE:
<223> OTHER INFORMATION: The nucleic acid was designed and synthesized.

<400> SEQUENCE: 7
gcaaggatcc gacgtttgtt gaaggcgata                                     30

<210> SEQ ID NO 8
<211> LENGTH: 30
<212> TYPE: DNA
<213> ORGANISM: Artificial Sequence
<220> FEATURE:
<223> OTHER INFORMATION: The nucleic acid was designed and synthesized.

<400> SEQUENCE: 8
ggcataaggg aattcggaat gccttgcgga                                     30

<210> SEQ ID NO 9
<211> LENGTH: 22
<212> TYPE: PRT
<213> ORGANISM: Artificial Sequence
<220> FEATURE:
<223> OTHER INFORMATION: The protein was designed and synthesized.

<400> SEQUENCE: 9

Ser Lys Ile Ser Gly Lys Trp Lys Ala Gln Lys Arg Phe Leu Lys Met
1               5                   10                  15

Ser Gly Asn Phe Gly Cys
            20

<210> SEQ ID NO 10
<211> LENGTH: 57
<212> TYPE: DNA
<213> ORGANISM: Artificial Sequence
```

```
<220> FEATURE:
<223> OTHER INFORMATION: The nucleic acid was designed and synthesized.

<400> SEQUENCE: 10
atgaagtgta tattatttaa atgggtactg tgcctggtgt aggctggagc tgcttcg      57

<210> SEQ ID NO 11
<211> LENGTH: 55
<212> TYPE: DNA
<213> ORGANISM: Artificial Sequence
<220> FEATURE:
<223> OTHER INFORMATION: The nucleic acid was designed and synthesized.

<400> SEQUENCE: 11
ttatgcctca gtcattatta aactgcactt cagcaacata tgaatatcct cctta        55
```